(12) United States Patent
Stiefel et al.

(10) Patent No.: US 10,300,171 B2
(45) Date of Patent: May 28, 2019

(54) RESORBABLE CROSSLINKED FORM STABLE MEMBRANE

(71) Applicant: GEISTLICH PHARMA AG, Wolhusen (CH)

(72) Inventors: Niklaus Stiefel, Lucerne (CH); Sergej Stenzel, Oftringen (CH); Raphael Kaufmann, Ballwil (CH)

(73) Assignee: Geistlich Pharma AG, Wolhusen (CH)

( * ) Notice: Subject to any disclaimer, the term of this patent is extended or adjusted under 35 U.S.C. 154(b) by 0 days.

(21) Appl. No.: 15/975,980

(22) Filed: May 10, 2018

(65) Prior Publication Data

US 2018/0256785 A1 Sep. 13, 2018

Related U.S. Application Data

(63) Continuation of application No. PCT/EP2016/079622, filed on Dec. 2, 2016.

(30) Foreign Application Priority Data

Dec. 4, 2015 (EP) ..................................... 15198070

(51) Int. Cl.
| | |
|---|---|
| A61L 27/58 | (2006.01) |
| A61L 27/24 | (2006.01) |
| A61F 2/28 | (2006.01) |
| A61C 8/02 | (2006.01) |
| A61L 27/46 | (2006.01) |

(52) U.S. Cl.
CPC ............... *A61L 27/46* (2013.01); *A61L 27/58* (2013.01); *A61L 2430/12* (2013.01)

(58) Field of Classification Search
None
See application file for complete search history.

(56) References Cited

U.S. PATENT DOCUMENTS

| | | | | |
|---|---|---|---|---|
| 2004/0258729 | A1* | 12/2004 | Czernuszka | A61L 27/227 424/426 |
| 2014/0193477 | A1* | 7/2014 | Chaikof | A61L 27/34 424/443 |

FOREIGN PATENT DOCUMENTS

| | | |
|---|---|---|
| CN | 101163512 A | 4/2008 |
| EP | 3233146 B1 | 5/2018 |
| JP | 07-088174 A | 4/1995 |
| JP | 11-199209 A | 7/1999 |
| JP | 2002-248119 A | 9/2002 |
| JP | 2012-515035 A | 7/2012 |

OTHER PUBLICATIONS

Jardelino et al., Acta Cirurgica Brasileira, 25(4), pp. 332-336. (Year: 2010).*
Teng, S. et al: "Three-Layered Membranes of Collagen/Hydroxyapatite and Chitosan for Guided Bone Regeneration", Journal of Biomedical Materials Research, Part B: Applied Biomaterials, vol. 87B, No. 1, 2008, pp. 132-138.
Roeder, B.A. et al: "Tensile Mechanical Properties of Three-Dimensional Type I Collagen Extracellular Matrices With Varied Microstructure", Journal of Biomechanical Engineering, vol. 124, No. 2, 2002, pp. 214-222.
Liao, S. et al: "A three-layered nano-carbonated hydroxyapatite/collagen/PLGA composite membrane for guided tissue regeneration", Biomaterials, vol. 26, No. 36, 2005, pp. 7564-7571.
Notification of Transmittal of the International Search Report and The Written Opinion of the International Searching Authority or the Declaration dated Feb. 10, 2017, cited in PCT/EP2016/079622, 11 pages.
First Notification of Office Action dated Sep. 25, 2018 in corresponding Chinese Application No. 201680069895.1, 7 pages.
Decision for Grant of Patent dated Sep. 10, 2018 in corresponding Korean Application No. 10-2018-7015487, 3 pages.
Notification of Reasons for Rejection dated Oct. 23, 2018 in corresponding Japanese Application No. 2018-528626, 3 pages.

\* cited by examiner

*Primary Examiner* — Abigail Vanhorn
(74) *Attorney, Agent, or Firm* — Rothwell, Figg, Ernest & Manbeck, P.C.

(57) ABSTRACT

A resorbable crosslinked form stable membrane containing a composite layer of collagen material and inorganic ceramic particles containing 1.5 to 3.5 weight parts of inorganic ceramic for 1 weight part of collagen material, sandwiched between two layers of elastic pretensed collagen material, wherein the elastic pretensed collagen material is collagen material that has been stretched such as to be in the linear/elastic region of the stress-strain curve, the collagen material comprising 50-100% (w/w) collagen and 0-50% (w/w) elastin.

19 Claims, 6 Drawing Sheets

RESORBABLE CROSSLINKED FORM STABLE MEMBRANE

CROSS-REFERENCE TO RELATED APPLICATIONS

This application is a continuation of International Application Number PCT/EP2016/079622, filed Dec. 2, 2016, which claims the benefit of European Patent Application No. 15198070.3, filed Dec. 4, 2015, the disclosures of which are incorporated by reference herein in their entireties.

FIELD OF THE INVENTION

The invention relates to a new resorbable crosslinked form stable membrane for use in the oral cavity, a process for preparing that membrane and the use thereof as implant to support bone formation, bone regeneration, bone repair and/or bone replacement at a non-containing dental bony defect site in a human or animal.

BACKGROUND OF THE INVENTION

In order to regenerate non-containing bony defects by bone formation, such as e.g. in horizontal or vertical augmentations in the maxilla or mandible, mechanical stabilization of the defect is required (Bendkowski 2005 "Space to Grow" The Dentist: 3; Merli, Migani et al. 2007 Int. J. Oral Maxillofac. Implants 22(3): 373-82; Burger 2010 J. Oral Maxillofac. Surg. 68(7): 1656-61; Louis 2010 Oral Maxillofac. Surg. Clin. North Am. 22(3): 353-68). Indeed, oral tissues are exposed to complex mechanical forces during mastication, swallowing, tongue movement, speech, tooth movement and orthodontic treatment. Especially during wound healing following surgical procedures, internal and external forces may occur, creating pressure, shear forces and bending moments upon. the regenerative device and newly formed tissue.

A form stable membrane resisting those forces is a useful means for bringing that mechanical stabilization.

It is known to use for that purpose Ti-meshes, Ti-plates or Ti-reinforced PTFE form stable membranes which have to be removed after bone regeneration during a second surgery. An example of a commercially available Ti-reinforced form stable membrane is the Cytoplast® membrane marketed by Osseogenies. However, the occurrence of dehiscences or other complications when using expanded Ti-reinforced membranes is reported to be high (Strietzel 2001 Mund Kiefer Gesichtschir. 5(1): 28-32; Merli, Migani et al. 2007 supra; Rocchietta, Fontana et al. 2008 J. Clin. Periodontol. 35(8 Suppl): 203-15).

Non reinforced PTFE membranes werewidely used prior the introduction of resorbable collagen membranes in 1996, but disappeared very fast after the introduction of collagen membranes.

To avoid the need of removal of a form stable membrane or meshes in a second surgery, a resorbable form stable membrane is of interest. Several resorbable form stable membranes or meshes have been described, essentially made from PLA (poly-lactic acid) or PLGA (poly-lactic-co-glycolic acid). Examples are notably (1) "Sonic Weld RX®" and "Resorb-X®" from KLS Martin, (2) "Guidor®" from Sunstar Americas, (3) the "Inion GTR System™" from Curasan and (4) "RapidSorb®" from Depuy Synthes. The disadvantage of those membranes is that during their in vivo hydrolytic degradation they release lactic and/or glycolic acid which cause tissue irritation and histological signs of a disturbed wound healing (Counts Whitman et al. 1998 Biomed. Mater. Res. 42(2): 303-11; Heinze 2004 Business briefing: Lobal Surgery: 4; Pilling, Mai et al. 2007 Br J. Oral Maxillofac. Surg. 45(6): 447-50).

To overcome PLGA/PLA associated wound healing problems, the use of autologous bone blocks from the patient and partly or completely purified bone blocks, such as e.g. Geistlich Bio-Oss® Block (Geistlich Pharma A.G.) or Puros® Allograft Block (RTI Surgical Inc.), is widely accepted. Autologous bone blocks have the disadvantage that they are harvested from a second site leading to more pain. (Esposito, Grusovin et al. 2009 Eur. J Oral Implantol. 2(3): 167-84)

To enable the use of autologous bone chips harvested during surgery, usually in combination with xenogenic bone graft particles, the so called bone shield technique was developed using autologous cortical bone from the mandibula (Khoury, Hadi et all. 2007 "Bone Augmentation in Oral Implantology", London, Quintessence). Disadvantages of this procedure are that it is extremely technique sensitive and that it is associated with second site morbidity and more pain. Further, bone shields are applied only laterally, therefore no mechanical protection is given from the coronal aspect of the defect. The term "bone shield" was used for advertising PLA/PLGA membranes as well as a partially demineralized cortical bone shield (Semi-Soft and Soft Lamina Osteobiol® from Tecnoss). The disadvantages of this demineralized bone shield are that bent bone shields have to be fixed always, that they are relatively thick compared to e.g. Ti-reinforced PTFE membranes and that they come only in round shapes with curved edges on the coronal aspect of the bony defect. For dentists, a 6-8 mm wide plateau in the coronal aspect of the ridge would be much more preferred (Wang and Al-Shammari 2002 Int. J. Periodontics Restorative Dent. 22(4): 335-43).

An attempt to combine uneventful healing and form stability is the resorbable form stable collagen membrane disclosed in U.S. Pat. No. 8,353,967-B2, which is prepared from a collagen suspension in 5-25% ethanol/water in a mould by freeze-drying and heating at 100 to 140° C. Such a membrane is manufactured by Osseous Technologies of America and marketed under the trade name "Zimmer CurV Preshaped Collagen Membrane" by Zimmer. That commercial membrane has weak form stability and a thickness of about 1.5 mm rising after incubation in saline to around about 2.3 mm; this may lead to a risk of a high dehiscence rate.

In summary the current solutions for are thus not fully satisfying for dentists or patients. Either a second surgery is necessary and/or there is a high risk of eventful wound healing. Solutions which are not associated with a high risk of eventful wound healing are either not form stable membranes, require a second surgery or have other disadvantages.

US 2013/0197662 discloses a process for fabricating a biomaterial comprising a) joining a porous collagen-based material with a non-porous collagen-based material by applying a controlled amount of a gel comprising collagen to a bonding surface of the non-porous collagen-based material, and contacting a surface of the porous collagen-based material with the gel applied to the bonding surface to partially hydrate a section of the porous material at the interface between materials; b) drying the gel to bond the materials together; and c) crosslinking the collagens in the bonding layers. The fabricated biomaterial obtained combines a porous collagen based material, which may be mineralized [0042], [0048], and a mechanically strong non-porous collagen-based material, thus providing a scaffold for regeneration of load-bearing tissues (notably meniscus, articular cartilage, tendons and ligaments), which has both porosity and mechanical strength, i.e. is able to resist compressional and tensional forces. Nothing is disclosed on the resistance to bending moments of that combined biomaterial or on the composition of the mineralized porous collagen-based material.

US 2014/0193477 teaches that in the fabrication of collagen mats from soluble collagen stretching the collagen prior to its crosslinking increases its mechanical strength, in particular the ultimate tensile strength (UTS), stiffness and elastic modulus (Young's modulus) (see in particular [0109], [0110]).

Langdon, Shari E et al., Biomaterials 1998, 20(2),137-153 CODEN and Chachra, Debbie et al., Biomaterials 1996, 17(19), 1865-1875 CODEN, disclose that stretching a pericardium derived membrane prior to its crosslinking increases its tensile strength and stiffness.

BRIEF SUMMARY OF THE INVENTION

The objective of the present invention is to provide a resorbable form stable membrane for use in the oral cavity, apt to resist to pressure, shear forces and bending moments such as to support bone formation, bone regeneration, bone repair and/or bone replacement at a non-containing bony defect site, notably in horizontal or vertical augmentations in the maxilla or mandible, which does not have the above drawbacks.

The objective is attained by the invention as defined in the appended claims.

The invention provides a resorbable crosslinked form stable membrane for use in the oral cavity which comprises a composite layer of collagen material and inorganic ceramic particles containing 1.5 to 3.5 weight parts of inorganic ceramic for 1 weight part of collagen material, sandwiched between two layers of elastic pretensed collagen material, the collagen material comprising 50-100% (w/w) collagen and 0-50% (w/w) elastin.

DETAILED DESCRIPTION OF THE INVENTION

The term "collagen material" here means a collagen-based material, which comprises 50-100% (w/w) collagen and 0-50% (w/w) elastin. The elastin content as used herein is measured by desmosine/iodesrnosine determination according to a modification of a known method involving hydrolysis and RP-HPLC (see e.g. Guida E. et al. 1990 *Development and validation of a high performance chromatography method for the determination of desmosines in tissues* in Journal of Chromatography or Rodriguqe P 2008 *Quantification of Mouse Lung Elastin During Prenatal Development* in The Open Respiratory Medicine Journal), which is incorporated by reference in its entirety. To determine the desmosine/isodesmosine content of dry elastin, the elastin of the collagen material is subjected to elastin isolation procedures as described by Starcher and Galione in 1976 (*Purification and Comparison of Elastin from Different Animal Species* in Analytical Biochemistry), which is incorporated by reference in its entirety.

That collagen material is suitably derived from tissues of natural origin which contain such proportions of collagen and elastin. Examples of such tissues include vertebrate, in particular mammalian (e.g. porcine, bovine, equine, ovine, caprine, lapine) peritoneum or pericardium membrane, placenta membrane, small intestine submucosa (SIS), dermis, dura mater, ligaments, tendons, diaphragm (Thoracic diaphragm), omentum, fascie of muscles or organs. Such tissues are preferably porcine, bovine or equine. An interesting tissue is a porcine, bovine or equine peritoneum membrane.

Usually the collagen is predominantly collagen type I, collagen type III or a mixture thereof. The collagen may also include a proportion of notably collagen type II, type IV, type VI or type VIII or any combination of those or any collagen types.

Preferably the collagen material contains 70-90% (w/w) (w/w) collagen and 30-10% (w/w) elastin.

An example of a suitable starting material for preparing such a collagen material is a collagen membrane from porcine, bovine or equine peritoneum or pericardium prepared by a process similar to that described in "Example" of EP-B1-1676592, or the membrane Geistlich Bio-Gide® (obtainable from Geistlich Pharma A.G., Switzerland) prepared from porcine peritoneum by such a process.

Preferably the collagen material is derived from a porcine, bovine or equine peritoneum or pericardium membrane, small intestine mucosa (SIS) or muscle fascie.

The collagen material is generally and preferably fibrous collagen material, either with a natural fibre structure or as cut collagen fibres.

However non fibrous collagen material, such as fibrils reconstituted from molecular collagen or crosslinked collagen fragments which have enough biocompatibility and resorbability, may also be used in the composite layer of collagen material and inorganic ceramic particles, or in the layers of elastic pretensed collagen material provided that collagen material possess sufficient mechanical stability in terms of Elastic modulus as well as maximal tensile strength (see below).

The term "resorbable" here means that the crosslinked form stable membrane is capable of being resorbed in vivo notably through the action of collagenases and elastases. A controlled in vivo resorbability of the crosslinked form stable membrane is essential to healing without excessive inflammation or dehiscence. The enzymatic degradation test using collagenase from *Clostridium histolicum* described in detail below (Example 4, 3) gives an excellent prediction of the in vivo resorbabilim All tested prototypes of the resorbable crosslinked form stable membrane of the invention tested showed at least 10% collagen degradation (as assessed by DC Protein assay using type I collagen as standard) after 4 hours, the rate of collagen degradation (lower than for the Geistlich Bio-Gide® membrane) being dependent on the crosslinking conditions used.

The term "crosslinked" means that the resorbable form stable membrane has been submitted to at least one step of crosslinking, usually chemical crosslinking (using e.g. EDC and NHS) or crosslinking by dehydrothermal treatment (DHT), that step being performed on the assembled composite layer of collagen material and inorganic ceramic particles sandwiched between two layers of elastic pretensed collagen material usually by chemical crosslinking (using e.g. EDC and NHS) or by dehydrothermal treatment (DHT). Optionally the composite layer of collagen material and inorganic ceramic particles has been crosslinked prior to its assembling into the membrane of the invention, usually by chemical crosslinking or by dehydrothermal treatment (DHT).

The term "form stable membrane for use in the oral cavity" means that the resorbable crosslinked membrane is capable of supporting bone formation, bone regeneration, bone repair and/or bone replacement at a non-containing dental bony defect site in a human or animal by providing a mechanical stabilization of the defect, i.e. resistance to the pressure, shear forces and bending moments that occur in the oral cavity. The form stability of the membrane of the invention is assessed by a 3-point uniaxial bending test described in detail below (in Example 4 2): That test is similar to the methods set forth in EN ISO178 and ASTM D6272-10, the membrane of the invention being submerged in PBS at a of 7.4 and a temperature of 37° C. That test showed that the membrane of the invention provides a substantially stronger stabilization than the competitive PLA membrane Resorb-X® (KLS Martin).

Generally, in that 3-point uniaxial bending test, the resorbable crosslinked form stable membrane resists to a force of at least 0.20 N, preferably at least 0.30 N, for 8 mm strain.

The term "layers of elastic pretensed collagen material" means that prior to their crosslinking the layers of collagen material have been submitted to a tensioning leading to an elongation or stretching of the initial size of the layers of collagen material from the toe region into the linear (also called elastic) region of the stress-strain curve (See Blayne A. Roder et al., 2002, Journal of Biomechanical Engineering, 124, 214-222, in particular FIG. 3, page 216, or FIG. 5 of the present application). Within this linear region, the elastic modulus is highest and therefore the highest stiffness can be achieved. That tensioning may be performed radially on the collagen material pieces, e.g. by springs. The forces to be applied for such a tensioning to lead to an elongation or stretching of the collagen material into the linear region of the stress-strain curve depend on the collagen material. When the collagen material is derived from porcine, bovine or equine peritoneum membrane, the tensioning leading to the linear region of the stress-stain curve of the collagen material may be performed radially on the collagen material pieces, by springs tensioned between 1 and 3 N, leading to an elongation or stretching of 40 to 100%, of the initial size of the layers of collagen material.

The term "elastic pretensed collagen material" thus means collagen material that has been stretched such as to be in the linear/elastic region of the stress-strain curve.

The elastic modulus (also called Young's modulus), i.e. the slope of the linear region of the stress-strain curve expressed in MPa, of the elastic pretensed collagen material is generally from 1 to 1000 MPa, preferably from 2 to 150 MPa, in particular from 5 to 80 MPa.

The presence of those two layers of "elastic pretensed collagen material" sandwiching the composite layer of collagen material and inorganic ceramic particles seems to be necessary for preventing the composite layer from breaking when the membrane is submitted to tensile, compressive, shear forces and bending moments.

Preferably one of the layers of elastic pretensed collagen material includes holes of 5 to 500 μm. When the membrane is in place that punctured layer of elastic pretensed collagen material will be oriented towards the bony defect, the holes allowing an easy invasion by the bone-forming cells into the inorganic ceramic-collagen composite material.

The inorganic ceramic is a biocompatible material that promotes bone regeneration such as hydroxyapatite or a natural bone mineral.

A well-known natural bone mineral that promotes bone growth in dental, periodontal and maxillofacial osseous defects is Geistlich Bio-Oss®, commercially available from Geistlich Pharma AG. That hydroxyapatite based bone mineral material is manufactured from natural bone by a process described in U.S. Pat. No. 5,167,961, which enables preservation of the trabecular architecture and nanocrystalline structure of the natural bone.

Preferably the inorganic ceramic is a hydroxyapatite based natural bone mineral, such as e.g. Geistlich Bio-Oss®.

The inorganic ceramic particles have generally a size of 50 to 600 μm, preferably of 150 to 500 μm, in particular of 250 to 400 μm.

The composite of collagen material and inorganic ceramic particles contains 1.5 to 3.5 weight parts, preferably 2,0 to 3.0 weight parts of inorganic ceramic for 1 weight part of collagen material.

Indeed, it has been unexpectedly found that below 1.5 weight part of inorganic ceramic for 1 weight part of collagen material or above 3.5 weight parts of inorganic ceramic for 1 weight part of collagen material, the membrane is not "form stable" as defined above and assessed by the 3-point uniaxial bending test described in detail below (in Example 4.2). The form stability is especially high when the composite of collagen material and inorganic ceramic particles contains 2.0 to 3.0 weight parts of inorganic ceramic for 1 weight part of collagen material.

The resorbable crosslinked form stable membrane of the invention is hydrophilic, being generally completely wetted by PBS in 5 to 10 minutes.

The resorbable crosslinked form stable membrane of the invention has cell adhesion properties similar to those of Geistlich Bio-Gide®, which is well known for its good healing properties with a low rate of dehiscence or excessive inflammation. This is indicative of good healing properties without adverse advents such as dehiscence or excessive inflammation.

Such good healing properties have been observed when implanting the crosslinked form stable membrane of the invention to protect bony defects created in the skull of rabbits, The thickness of the resorbable crosslinked form stable membrane of the invention is usually from 0.5 to 2.5 mm, preferably 1.0 to 2.0 mm, in particular 1.2 to 1.8 mm.

Figure 1:
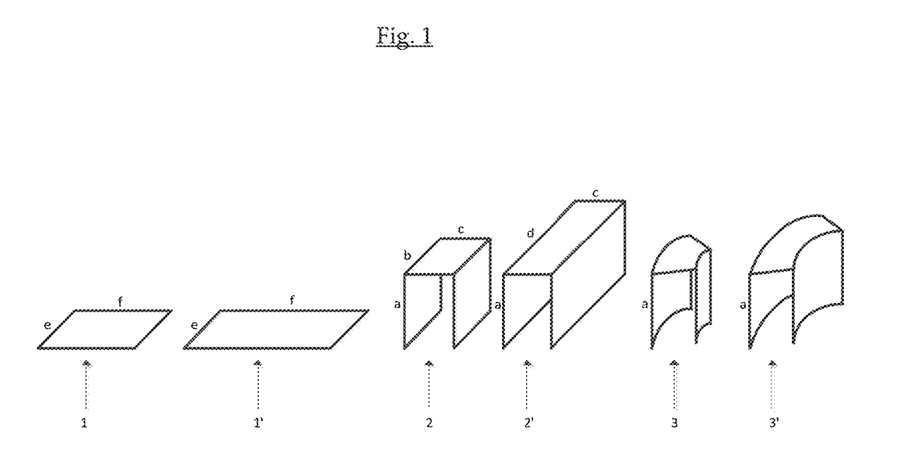
FIG. 1 represents typical shapes and typical dimensions of resorbable crosslinked form stable membranes according to the invention. Those membranes may be flat (1), (1'), U-shaped straight (2), (2') or U-shaped curved (3), (3') corresponding to the alveolar spaces of 1 to 3 teeth (incisors, canine, premolar or molars) situated at the front, in the left-hand side or right-hand side curvature or at the rear of the denture.

Typical shapes and typical dimensions of the resorbable crosslinked form stable membrane of the invention are represented in FIG. 1.

The invention also relates to the above resorbable crosslinked form stable for use as an implant to support bone formation, bone regeneration, bone repair and/or bone replacement at a non-containing dental bony defect site in a human or animal.

The invention also concerns a process for preparing the above defined resorbable crosslinked form stable membrane which comprises a composite layer of collagen material and inorganic ceramic particles sandwiched between two layers of elastic pretensed collagen material, comprising the steps of:

(a) Preparing a composite layer of collagen material and inorganic ceramic particles, optionally crosslinking that composite layer, (b) Assembling and glueing the composite layer of collagen material and inorganic ceramic particles between two layers of collagen material submitted to tensioning leading to a stretching of the collagen material in the linear region of the stress-strain curve, thereby giving a composite layer of collagen material and inorganic ceramic particles sandwiched between two layers of elastic pretensed collagen. material, and (c) Crosslinking that composite layer of collagen material and inorganic ceramic particles sandwiched between two layers of elastic pretensed collagen material, followed by a hydrophilic making treatment.

Step (a) may be performed by:

Producing, as inorganic ceramic particles, hydroxyapatite bone mineral particles from cortical or cancellous bone by a process similar to that described in U.S. Pat. No. 5,417,975 or alternatively grinding Geistlich Bio-Oss Small Granules (available for Geistlich Pharma AG) into smaller particles, and submitting those particles to a sieving in the desired range (e.g. of 150 to 500 μm or 250 to 400 μm), thereby giving sieved hydroxyapatite bone mineral particles.

Preparing fibrous collagen material by
submitting collagen rich tissue from porcine, bovine or equine peritoneum or pericardium to a process similar to that described in Example of EP-B1-1676592, or alternatively starting from the Geistlich Bio-Gide membrane (available for Geistlich Pharma AG) obtained from porcine peritoneum by such a process or from the intermediate product obtained before sterilization in the industrial production of the Geistlich Bio-Gide membrane, called here the unsterile Geistlich Bio-Gide membrane, cutting (e.g. with scissors) pieces of the thus obtained collagen fibrous tissue, mixing those pieces of cut collagen fibrous tissues with dry ice using a knife mill, thus giving cut collagen fibres, cutting pieces of collagen fibrous tissues with a cutting mill with a sieve, thus giving a sieved fraction of collagen fibre fragments.

Preparing a composite layer of fibrous collagen material and hydroxyapatite bone mineral particles by
mixing and shaking in phosphate buffer saline PBS, 0 to 40% by weight of the cut collagen fibres and 60 to 100% by weight of the sieved fraction of collagen fibre fragments obtained above, adding from 1.5 to 3.5 weight parts, in particular 2.0 to 3.0 weight parts, of the sieved hydroxyapatite bone mineral particles obtained above to 1 weight part of the fibrous collagen obtained in the above paragraph, centrifuging at 2000 to 6000 xg, preferably 3000 to 5000 xg, pouring the obtained pellet into a rectangular form and forming a plate using a spatula. The composite layer of fibrous collagen material and hydroxyapatite bone mineral particles obtained is dried in a vacuum oven.

Crosslinking the dried composite layer of collagen material and inorganic ceramic particles at the end of (a) is not necessary but has the advantage that it facilitates the handling of that composite layer during step (b).

That crosslinking may be performed using chemicals or by dehydrothermal treatment (DHT).

Crosslinking with chemicals may be performed using any pharmaceutically acceptable crosslinking agent capable of giving to the crosslinked form stable membrane the required mechanical strength. Suitable such crosslinking agents include gluteraldehyde, glyxoal, formaldehyde, acetaldehyde, 1,4-butane diglycidyl ether (MIDGE), N-sulfosuccinimidyl-6-(4'-azido-2'-nitrophenylamino) hexanoate, hexamethylene diisocyanate (HMDC) cynamide, diphenylphosphorylazide, genipin, EDC (1-ethyl-3-(3-dimethylaminopropyl)-carbodiimide) and a mixture of EDC and NHS (N-hydoxysuccinimi de).

Crosslinking using chemicals is conveniently performed using a mixture of EDC and NHS.

In that case, the dried composite layer of fibrous collagen material and hydroxyapatite bone mineral particles obtained above may be crosslinked in 10-400 mM EDC and 13-520 mM NHS in in a 0.1 M MES (2-(N-morpholino)-ethanesulfonic acid) and 40% ethanol solution at pH 5.5 for 1 to 3 hours at room temperature. The reaction is may be then stopped by incubating the prototypes twice in 0.1 M Na2HPO4 buffer at pH 9.5 for 1 to 3 hours, Polar residuals may be removed by incubating the prototypes for 1 hour in a 1 M sodium chloride solution and twice for an hour in a 2 M sodium chloride solution. The chemically crosslinked prototypes may be washed a total of 8 times for 30-60 minutes in distilled water. Drying may then be performed by carrying out by immersion in ethanol for 15 minutes a total of 5 times, followed by three times diethylether treatment for 5 minutes and subsequent drying at 10 mbar and 40° C. over night, or by lyophilisation (freezing below −5° C. and drying by conventional lyophilisation treatment).

Alternatively, cross-linking was performed by dehydrothermal treatment (DHT) at 0.1-10 mbar and 80-160° C. for 1-4 days. In this case no subsequent drying method is necessary.

Figure 2:
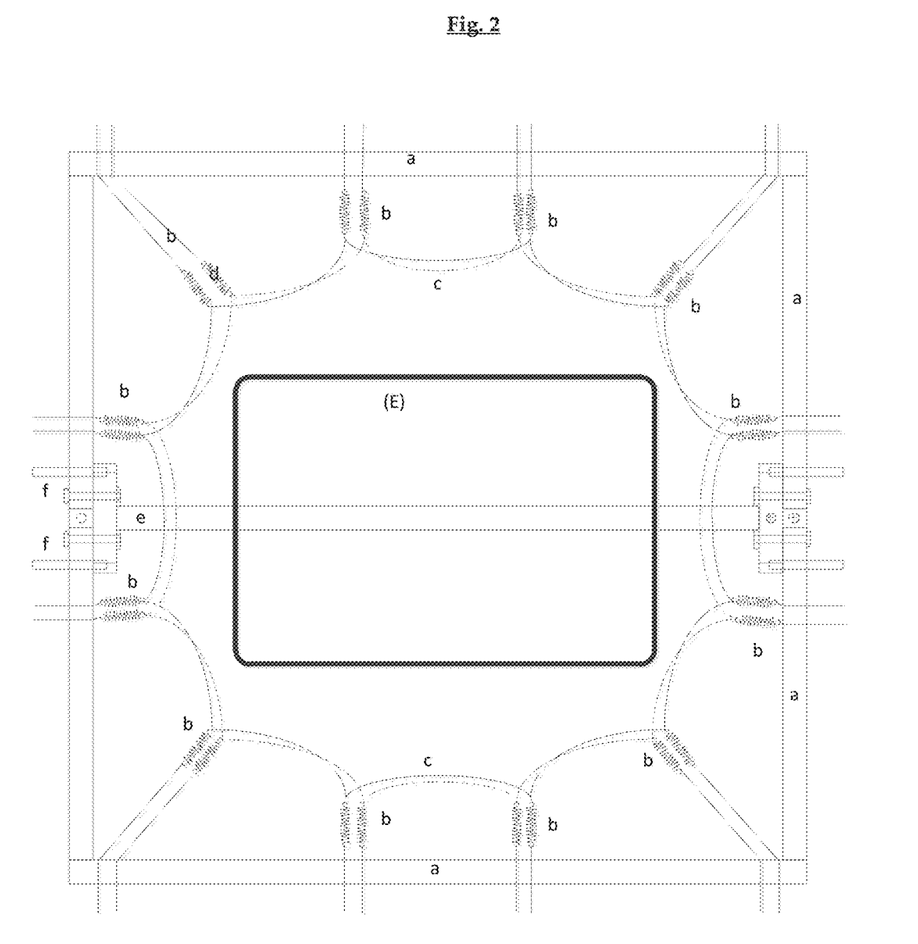
FIG. 2 is a schematic view of equipment suitable for enabling the tensioning of the polymer layers prior to their assembling into a flat or U-shaped form stable membrane of the invention.
Figure 3:
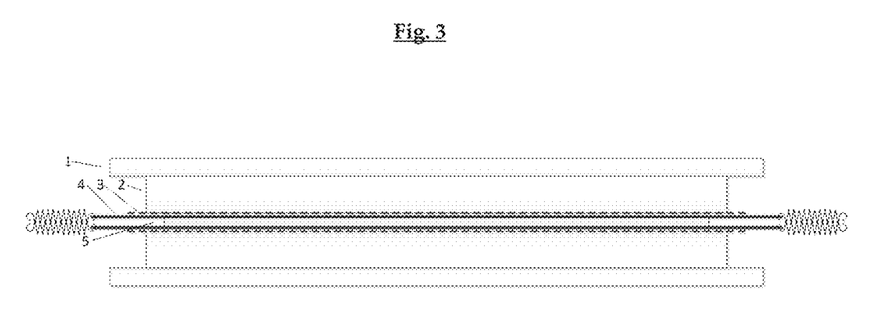
FIG. 3 represents the assembly of a flat form stable membrane, wherein (1) is a steel plate, (2) is a compressed polyurethane sponge, (3) is a polyamide net, (4) is a layer of elastic pretensed collagen and (5) is a crosslinked hydroxyapatite-collagen plate.

Step (b) may be performed by:

Preparing a collagen fiber glue by
mixing the above sieved fraction of collagen fragments in an aqueous $H_3PO_4$ solution of pH 3.5 at a concentration of 3% using a high pressure homogenizer at 1500-2000 bar, that mixing being repeated several times, neutralizing the resulting slurry to pH 7.0 by adding a sodium hydroxide solution, concentrating by lyophilization the collagen and homogenizing the latter by knife milling, preparing the collagen fibre glue from the slurry obtained as a 240% solution in phosphate buffer saline PBS of pH 7.4 by heating to 60° C. until no further particles were visible, and Using e.g. an equipment similar to that of FIG. 2, submitting two prewetted layers of collagen material to tensioning leading to a stretching of the collagen material in the linear region of the stress-strain curve, thereby giving two layers of wet elastic pretensed collagen material, inserting the composite layer of collagen material and inorganic ceramic particles obtained in (a) imbibed with the above collagen fibre glue between the above two layers of wet elastic pretensed collagen material, using e.g. an equipment similar to that of FIG. 3, pressing those two layers of wet elastic pretensed collagen material against that composite layer of collagen material and inorganic ceramic particles imbibed with the collagen fibre glue, and drying the composite layer of collagen material and inorganic ceramic particles sandwiched between two layers of wet elastic pretensed collagen material at a temperature of 35 to 45° C. under reduced pressure (e.g. from 20 to 1 mbar).

In the above described procedure, one of the prewetted layers of collagen material may have been subjected to a puncturing with needles such as to include holes of 5 to 500 μm.

In step (c), crosslinking that composite layer of collagen material and inorganic ceramic particles sandwiched between two layers of elastic pretensed collagen material, may be performed using chemicals (using e.g. EDC and NHS) or by dehydrothermal treatment DHT.

The chemical crosslinking may be performed using any pharmaceutically acceptable crosslinking agent capable of giving to the crosslinked formstable membrane the required mechanical strength. Suitable such crosslinking agents include gluteraldehyde, glyoxal, formaldehyde, acetaldehyde, 1,4-butane diglycidyl ether (BDDGE), N-sulfosuccinimidyl-6-(4'-azido-2'-nitrophenylamino) hexanoate, hexamethylene diisocyanate (HMDC), cynamide, diphenylphosphorylazide, genipin, EDC (1-ethyl-3-(3-dimethylaminopropyl)-carbodiimide) and a mixture of EDC and NHS (N-hydoxysuccinimide).

The crosslinking using chemicals is conveniently performed using a mixture of EDC and NHS.

In that case, the dried composite layer of fibrous collagen material and hydroxyapatite bone mineral particles obtained above may be crosslinked in 10-400 mM EDC and 13-520 mM NHS in in a 0.1 M MES (2-(N-morpholino)-ethanesulfonic acid) and 40% ethanol solution at pH 5.5 for 1 to 3 hours at room temperature. The reaction is may be then stopped by incubating the prototypes twice in 0.1 M Na2HPO4 buffer at pH 9.5 for 1 to 3 hours. Polar residuals may be removed by incubating the prototypes for 1 hour in a 1 M sodium chloride solution and twice for an hour in a 2 M sodium chloride solution. The chemically crosslinked prototypes may be washed a total of 8 times for 30-60 minutes in distilled water. Dehydration and drying may then be performed by immersion in ethanol for 15 min. a total of 5 times followed by carrying out three times diethylether treatment for 5 minutes and subsequent drying at 10 mbar and 40° C. for 30 minutes, or by lyophilisation (freezing below −10° C. and drying by conventional lyophilisation treatment) without solvent treatment.

Alternatively, cross-linking was performed by dehydrothermal treatment (DHT) at 0.1-10 mbar and 80-160° C. for 1-4 days. In this case no subsequent drying method is necessary.

The hydrophilic making treatment of step c) generally comprises immersing the crosslinked composite layer of collagen material and inorganic ceramic particles sandwiched between two layers of elastic pretensed collagen material hydrophilic into a physiologically acceptable salt solution such as a sodium chloride solution, preferably a 100-300 g/l, in particular a 150-250 g/l sodium chloride solution.

Preferably the hydrophilic making treatment comprises immersing the crosslinked composite layer of collagen material and inorganic ceramic particles sandwiched between two layers of elastic pretensed collagen material hydrophilic into a sodium chloride solution.

The resorbable crosslinked form stable membrane of the invention may be sterilized by X-ray, beta-ray or gamma irradiation.

BRIEF DESCRIPTION OF THE DRAWINGS

The invention will be described in further detail hereinafter with reference to illustrative examples of preferred embodiments of the invention and the accompanying drawing figures, in which.

The size of the anterior products is similar to that of the posterior products, the radius of the curvature being such as to conform to the alveolar ridge. Typical dimensions are a=5-20 nm, b=8-20 mm, c=6-10 mm, d=25-40 mm, e=15 mm, f=20-40 mm.

The following examples illustrate the invention without limiting its scope.

EXAMPLE 1

Preparation of the Raw Materials

Preparation of Hydroxyapatite Fine Particles Having a Size of 250 to 400 μm (A) Hydroxyapatite bone mineral fine particles were produced from cortical or cancellous bone as described in Examples 1 to 4 of U.S. Pat. No. 5,417,975, using an additional sieving step between 250 and 400 μm.

Alternatively, hydroxyapatite bone mineral fine particles were produced by grinding Geistlich Bio-Oss® Small Granules (available from Geistlich Pharma AG, CH-6110, Switzerland) by careful impactation using a pistol and an additional sieving step between 250 and 400 μm.

The hydroxyapatite bone mineral fine particles having a size of 250 to 400 μm prepared above (A) were stored in glass bottles until use.

Preparation of Collagen Fibres (B)

As described in "Example" of EP-B1-1676592, peritoneal membranes from young pigs were completely freed from flesh and grease by mechanical means, washed under running water and treated with 2% NaOH solution for 12 hours. The membranes were then washed under running water and acidified with 0.5% HCl. After the material had been acidified through its entire thickness(for about 15 minutes) the material was washed with water until a pH of 3.5 was obtained. The material was then shrunk with 7% saline solution, neutralised with 1% $NaHCO_3$ solution and washed under running water. The material was then dehydrated with acetone and degreased with n-hexane and dried using ethanol ether. 2×2 cm pieces of the collagen membranes thus obtained were cut by hand using scissors.

Alternatively, 2×2 cm pieces of the Geistlich Bio-Gide® membrane (available from Geistlich Pharma AG) were cut by hand using scissors.

1 g of the 2×2 cm pieces of the collagen membranes obtained above was mixed with 200 ml of dry ice and mixed in a knife mill (Retsch® Grindomix) at 5000 rpm until no blockage occurred. The speed was then increased to 6000, 7000, 9000 and 10,000 rpm for 20 to 30 seconds, each time adding 50 ml of dry ice.

The dry ice was evaporated and the collagen fibres thus obtained B e stored in Minigrip plastic wraps until further use.

Preparation of Cutting Mill Collagen Fibre Segments (C)

The 2×2 cm collagen fibre pieces obtained above were cut in a cutting mill with a 0.8 mm sieve at 1500 rpm, giving a sieved fraction of cutting mill collagen fibre segments (C).

Preparation of a Collagen Fibre Glue (D)

The sieved fraction of cutting mill collagen fibre segments (C) was mixed in water to obtain a solution of 3%, the pH was set to 3.5 by adding phosphoric acid $H_3PO_4$ and the suspension was high pressure homogenized at 1500-2000 bar, this being repeated 3 to 5 times.

The resulting slurry was neutralized to about pH 7 by adding a sodium hydroxide solution NaOH and gelled overnight at 4° C. The collagen was concentrated by lyophilisation at −10° C. and 0.310 mbar after freezing for 4 hours at −40° C. and homogenized by knife milling.

The collagen fibre glue (D) was prepared from the slurry obtained as a 2-10% solution in phosphate buffered saline, pH 7.4 by heating to 60° C. until no further particles were visible.

EXAMPLE 2

Preparation of an Optionally Crosslinked Hydroxyapatite/Collagen Plate (E)

4 g of collagen fibres (B) and 6 g of cutting mill collagen fibre segments (C) prepared in Example 1 were mixed with 140 g of phosphate buffered saline and shaked in a cocktail mixer. In another example, collagen fibres were substituted completely by cutting mill collagen fibre segments.

20 g hydroxyapatite fine particles (A) prepared in Example 1 were added and mixed by hand.

34.14 g of this mixture were centrifuged at 7000 g (7000 times the acceleration of gravity) for 2 minutes.

The pellet was poured between two polyamide-nets (of pore size 21 μm and a total of 17% of open structure) in a flat rectangular form of 8×12 cm and the matter was condensed by removing excess water with a laboratory spoon. The plates obtained were compressed at a pressure of 1-1.7 kPa and dried in a vacuum oven at 30° C./50 mbar for 2 hours, then at 30° C./1.0 mbar for 8 hours. The polyamide-nets were removed.

Optional Crosslinking of the Hydroxyapatite-collagen Plate

To facilitate handling of the hydroxyapatite-collagen plate, the latter was crosslinked chemically or by dehydrothermal treatment (DHT).

Chemical cross-linking of the collagen with EDC/NHS was performed, leading to an increase of overall stability of the hydroxyapatite-collagen plate plates. The dried plates were then cross-linked in 10-400 mM EDC and 13-520 mM NHS in 0.1 M MES (2-(N-morpholino)-ethanesulfonic acid) and 40% ethanol at pH 5.5 for 2 hours at room temperature.

The reaction was stopped by incubating the prototypes twice in 0.1 mol/l $Na_2HPO_4$ buffer at pH 9.5 for an hour. Polar residuals were removed by incubating the prototypes for 1 hour in a 1 mol/l sodium chloride solution and twice for an hour in a 2 mol/l sodium chloride solution. The chemically crosslinked prototypes were washed a total of 8 times for 30-60 minutes in distilled water, then dehydrated by immersion in ethanol for 15 minutes a total of 5 times. Drying was then performed by carrying out three times diethylether treatment for 5 minutes and subsequent drying at 10 mbar and 40° C. for 30 minutes, or by lyophilisation (freezing below −10 ° C. and drying by conventional lyophilisation treatment).

Alternatively, cross-linking was performed by dehydrothermal treatment (DHT) at 0.1-10 mbar and 80-120° C. for 1-4 days. In this case no subsequent drying method was necessary.

EXAMPLE 3

Preparation of a Resorbable Crosslinked Form Stable Membrane (M) by Assembling and Gluing Two Elastic Pretensed Collagen Layers on the Two Opposite Faces of the Hydroxyapatite/collagen Plates (E)

The following description will be better understood by referring to FIGS. 2 and 3. The assembly of a flat or U-shaped prototype requires the use of fixed or bendable frames enabling the tensioning of the layers of collagen material.

Forming of Flat or U-shaped Prototypes (F)

FIG. 2 is a schematic view of equipment suitable for enabling the tensioning of the layers of collagen material prior to their assembling into a flat or U-formed form stable membrane of the invention.

That equipment consists of a frame (a), which can be made of any suitable material, e.g. steel or aluminum. The main purpose for the frame is to anchor the springs (b), which tension the two wet collagen layers (c). The hydroxyapatite/collagen plate (E) was positioned in between the two collagen layers (c).

If a U-shaped resorbable crosslinked form stable membrane is desired, a negative form (e) for bending the collagen plate (E) and frames with hinges (1) are used, thus leading to U-shaped straight prototypes.

Collagen material layers of unsterile Geistlich Bio-tide Collagen layers were pretensed by elongating or stretching 40 to 100% of initial length through tensioning each spring by 2-3 N, such as to be in the linear region of the stress-curve of the collagen material. Within this linear region, the elastic modulus is highest and therefore the highest stiffness is achieved Due to the viscoelastic nature of collagenous tissues, wet and tensioned materials were kept for approximately 30 minutes in tensioned state, Due to the relaxing of the pretensed collagen membrane, the springs were tensioned again to 1-3 N, such as to be in the linear region of the stress-curve of the collagen material.

Two round pieces of collagen with a diameter of 10 cm cut from unsterile Geistlich Bio-Gide® collagen membrane were used, one of which was punctured with a needle drum containing 50 needles per c with a shaft diameter of 0.88 mm. Those two round pieces of collagen were wetted and tensioned in a radial manner by 12 springs each tensioned to 1-3 N, leading to an elongation of 40-100% of the initial size of the collagen pieces.

Upon completion of this step, the hydroxyapatite/collagenplates (E) were wetted on both faces with the collagen fibre glue (C) and then, the hydroxyapatite/collagen plate was placed between the two elastic pretensed collagen layers. The central bar (e) as well as the hinges (f) are necessary to produce U-shaped prototypes (see below).

The elastic pretensed membranes were placed on a heating plate and prewarmed to 40° C.

The cross-linked Bio-Oss plate (E) obtained in Example 2 was shortly submerged in prewarmed collagen fiber glue (D) and placed between the two elastic pretensed collagen membranes.

Polyamide nets, as well as sponges (of thickness 5 cm, density of approx. 20-25 mg/cm$^3$, containing interconnected pores, made of polyurethane), were placed on both sides, compressed by 50-95 leading to compression pressures of up to 120 kPa.

See FIG. 3, which represents the assembly of a flat form stable membrane, wherein (1) is a steel plate, (2) is a compressed polyurethane sponge, (3) is a polyamide net, (4) is a layer of elastic pretensed collagen and (5) is a cross-linked hydroxyapatite-collagen plate .

Subsequently, the construct was dried in a vacuum oven at 40° C. with a steady decrease in air pressure down to 10 mbar for a total of 32 hours.

Forming of U-shaped Prototypes

The skilled person will readily adapt the apparatus of FIGS. 2 and 3 and the method described above to the forming of U-shaped prototypes straight or curved, by bending the construct over an appropriate negative form and replacing one of the sponges by a thinner polyurethane sponge or a fibre free paper towel.

Cross-linking of Flat or U-shaped Prototypes (G)

Flat or U-shaped prototypes (F) were cut into the desired dimensions using scissors or a small circular saw. The prototypes were then crosslinked chemically or by dehydrothermal treatment (DHT).

Chemical crosslinking was performed in 0.1 mol/L MES buffer at pH 5.5 and an ethanol content of 40 Vol-% at concentration of EDC and NHS of 10 to 400 mM and 13 to 520 mM respectively. The prototype concentration in the cross-linking solution was 10%. To enable homogenous cross-linking, plates were initially treated under vacuum (<40 mbar) and the cross-linking reaction was carried out at 4° C. for 2 hours, all buffers being precooled to this temperature.

The reaction was stopped by incubating the prototypes twice in 0.1 mol/l Na$_2$HPO$_4$ buffer at pH 9.5 for an hour. Polar residuals were removed by incubating the prototypes for 1 hour in a 1 mol/l NaCl solution and twice for an hour in a 2 mol/l NaCl solution. Prototypes were washed a total of 8 times for 30-60 minutes in distilled water. Dehydration and drying was then performed by carrying out 5 times ethanol treatment for 15 minutes and three times diethylether treatment for 5 minutes and subsequent drying at 10 mbar and 40° C. overnight or until the product was completely dry, or by conventional lyophilisation (freezing below −10° C. and drying by conventional lyophilisation treatment) of the not by solvent treated product.

Alternatively, cross-linking was performed by dehydrotherrnal treatment (DHT) at 0.1-10 mbar at 80-160° C. for 1-4 days. In this case no subsequent drying method was necessary.

Prototypes obtained by the above described methods are wetted in saline or PBS within an hour or two. To allow wetting within 10 min, prototypes are rewetted in distilled water for approximately 1 to 2 hours. At this time the perforation of one side with the above described needle drum is possible too. Sodium chloride is applied by incubating the prototypes three times for 40 min in a 200 g/l NaCl solution. The sodium chloride is precipitated as described below (H).

Drying of Cross-linked Flat or U-shaped Prototypes (H)

The crosslinked prototypes were dehydrated by immersion in ethanol for 15 minutes a total of 5 times. They were then dried by either solvent drying (three times diethylether treatment for 5 minutes and subsequent drying at 10 mbar and 40° C.) or conventional lyophilisation (freezing below −10° C. and drying by conventional lyophilisation treatment).

The thickness of the crosslinked form stable membrane of the different prototypes in wet state was from 1.0 to 2.0 mm, for most of them from 1.2 to 1.8 mm.

The dried prototypes were optionally sterilized by x-ray-irradiation at 27-33 kGy.

EXAMPLE 4

Properties of the Resorbable Crosslinked Form Stable Membrane

The following characteristics of the resorbable crosslinked form stable membrane obtained in Example 3 were determined: (1) Wettability in PBS, (2) Mechanical strength, (3) Enzymatic degradation using collagenase from *Clostridium histolyticum* and (4) Cell adhesion (5) Measurement of the elongation of the elastic pretensed collagen material layers (6) Measurement of the thickness of the collagen-hydroxyapatite plates and final prototypes (1) Wettability in PBS The time of complete wetting in PBS (Phosphate buffer saline) assessed visually was observed to be between 5 and 10 minutes for the different prototypes of the resorbable crosslinked form stable membrane, that time depending mainly on the treatment with sodium chloride prior to dehydration with ethanol and drying.

(2) Mechanical Strength

The form stability of the membrane of the invention was assessed by a 3-point uniaxial bending test which is similar to the methods described in EN ISO 178 and ASTM D6272-10, the membrane of the invention being submerged in PBS at a pH of 7.4 and a temperature of 37° C.

This test was considered most useful, because every form stable membrane designed to mechanically stabilize a bony defect at a non-containing site will experience bending moments. Therefore, 3- or 4-point bending can be used as a test to characterize the used materials and additionally to compare different products with e.g. different thicknesses. For material characterization, the bending modulus is the most suitable parameter. However, to compare different products which have different thicknesses, the maximal force after 8-10 mm of indentation is more relevant and therefore used, to characterize the product.

In the a 3-point uniaxial bending test used, the specimens were cut to a size of 50×13 mm and incubated in PBS at 37° C. until complete wetting as visually observed. Mechanical testing was conducted at 5 mm per minutes in a 3-point bending apparatus with a support span width of 26 mm and a radius of 5 mm of each supporting structure. The bending module was calculated within 1 and 5% bending strain. The resulting maximal forces were read out after lowering the central indenter between 8 and 10 mm.

The test was performed for a membrane of the invention of thickness 1.5 mm crosslinked by EDC/NHS, a membrane of the invention of thickness 1.6 mm crosslinked by DHT and the PLA membrane Resorb-X® from KLS Martin of thickness 0.137 mm.

Figure 4:
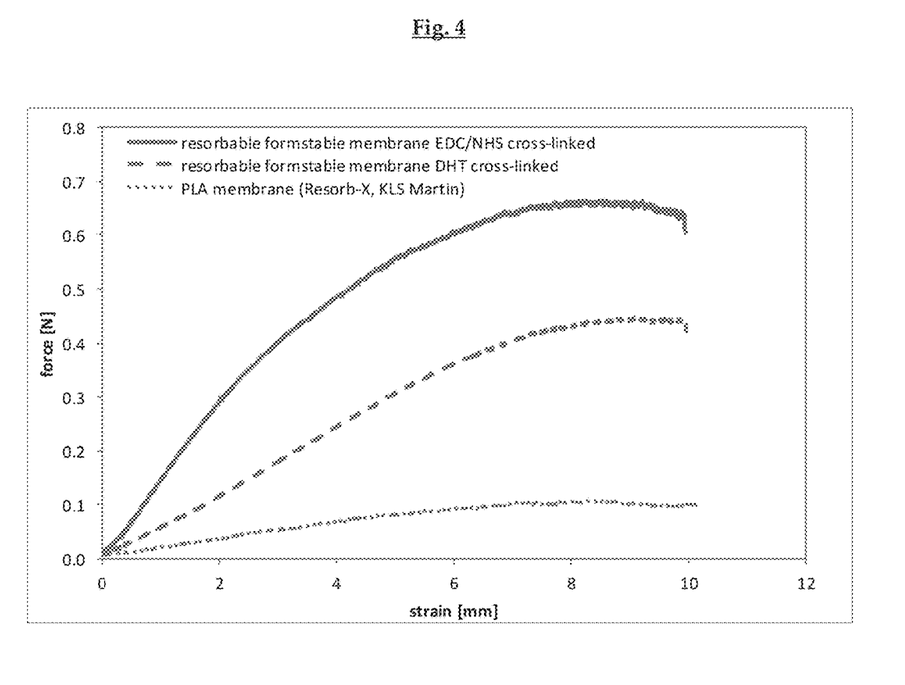
FIG. 4 represents the variation of the force as a function of the strain in a 3-point bending analysis test for the resorbable form stable membrane of the invention crosslinked by EDC/NHS or DHT in comparison to the PLA membrane Resorb-X® (KLS Martin).

FIG. 4, which represents the variation of the force as a function of the strain for those membranes, shows that the mechanical stability of membrane of the invention crosslinked by EDC NHS (about 0.65 N for 8 mm strain) or crosslinked by DHT (about 0.40 N for 8 mm strain) is substantially superior to that of the PLA membrane Resorb-X® (about 0.10 N for 8 mm strain). The membrane of the invention will thus better stabilize the bony defect at a non-containing site.

(3) Enzymatic Degradation Test Using Collagenase from *Clostridium histolyticum*

In the human body collagens are degraded by human tissue matrix-metalloproteinase (MMP), cathepsins and putatively by some serine proteinases. Best studied are the MMPs where collagenases (notably MMP-1, MMP-8, MMP-13 and MMP-18) are the most important enzymes for direct collagen degradation (Lauer-Fields et al. 2002 *Matrix metalloproteinases and collagen catabolism* in Biopolymers Peptide Science Section and Song et al. 2006 *Matrix metalloproteinase dependent and independent collagen degradation* in Frontiers in Bioscience).

Collagenase capability to degrade collagen tissues and membranes depends on the substrate flexibility and collagen type, MMP active sites and MMP exosites. Collagenases align at the triple helical collagen, unwind it and subsequently cleave it (Song et al. 2006, see above).

With the view of overcoming differences in degradation between the different collagen types, collagenase degradation of collagen is often assessed using* collagenase from *Clostridium histolyticum* which has a high catalytic speed (Kadler et al. 2007 *Collagen at a glance* in J Cell Sci.). Generally, a natural collagen product degrades faster than a chemically cross-linked collagen product.

In this test the collagen products (samples of the resorbable cross-linked formstable membrane at 1 mg/ml collagen) were incubated at 37° C. with 50 units/ml from *Clostridium histolyticum* (one unit being defined as liberating peptides from collagen from bovine Achilles tendon equivalent in ninhydrin color to 1.0 micromole of leucine in 5 hours at pH 7.4 at 37° C. in the presence of calcium ions) in a calcium containing Tris-buffer and the degradation of the collagen matrix was measured visually and with the "DC Protein Assay" from Bio-Rad Laboratories (Hercules, USA, Order Nr. 500-0116) using Collagen Type I as reference material. The collagen concentration was determined using a microwellplate spectrometer (Infinite M200, available from Tecan).

All prototypes of the resorbable crosslinked form stable membrane of the invention showed at least 10% collagen degradation (as assessed by DC Protein assay using collagen type I as standard.) after 4 hours, the rate of collagen degradation (lower than for the Geistlich Bio-tide® membrane) being dependent on the crosslinking conditions used.

(4) Cell Adhesion

Cell adhesion to different membranes was assessed by first seeding 8 mm membrane punches with 100,000 human gingival fibroblasts previously labelled with a fluorescent, lipophilic dye, incubating for 24 hours in PBS at 37° C., removing non-adherent cells by washing the membranes in PBS, lysing adherent cells and quantifying them by measuring fluorescence at 485 nm. Fluorescence was normalized to a standard curve established with cell-seeded membrane punches that were not washed prior to lysis.

Figure 5:
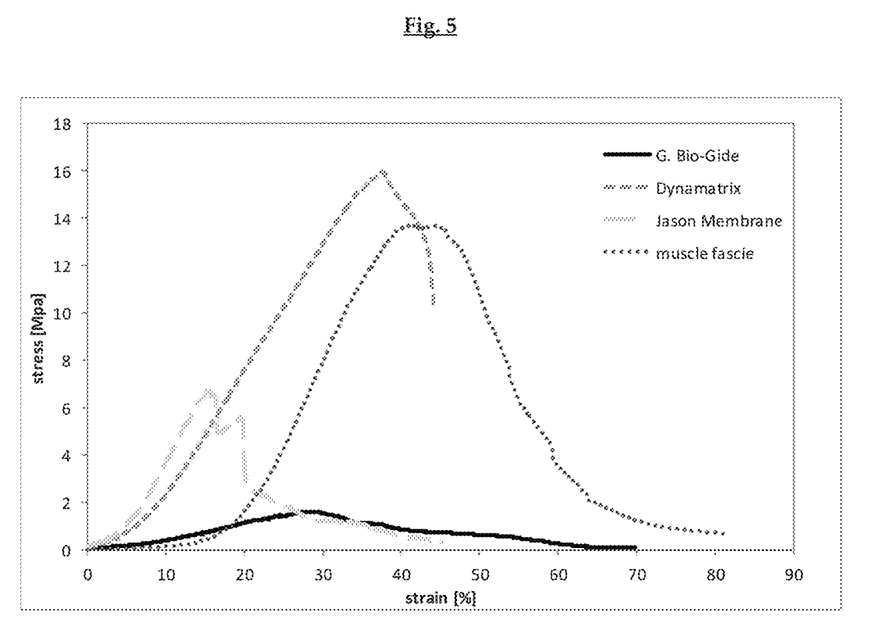
FIG. 5 represents the stress-strain curves of a few commercially available, wet and sterile collagen materials that could be used in the layers of elastic pretensed collagen material of the resorbable crosslinked form stable membranes according to the invention, namely porcine peritoneum derived Geistlich Bio-Gide® collagen membrane (Geistlich Pharma AG), porcine pericardium derived Jason® collagen membrane (aap Biomaterials/Botiss) and porcine SIS derived Dynamatrix® collagen membrane (Cook Biotech Inc.), and a collagen material derived from muscle fascie. In each of those stress-curves there is a toe region characterized by large strains upon minimal values of stress, a linear or elastic region characterized by a linear increase in strain per unit stress and a failure region characterized by rupture of polymeric fibres. In the stress-stain curves represented in this figure, the elastic modulus (or Young's modulus, i.e. the slope of the linear region of the stress-strain curve) is about 8 MPa for the Geistlich Bio-Gide® membrane, about 64 MPa for the Jason membrane, about 54 MPa for the Dynamatrix® membrane and about 56 MPa for the collagen material derived from muscle fascie
Figure 6:
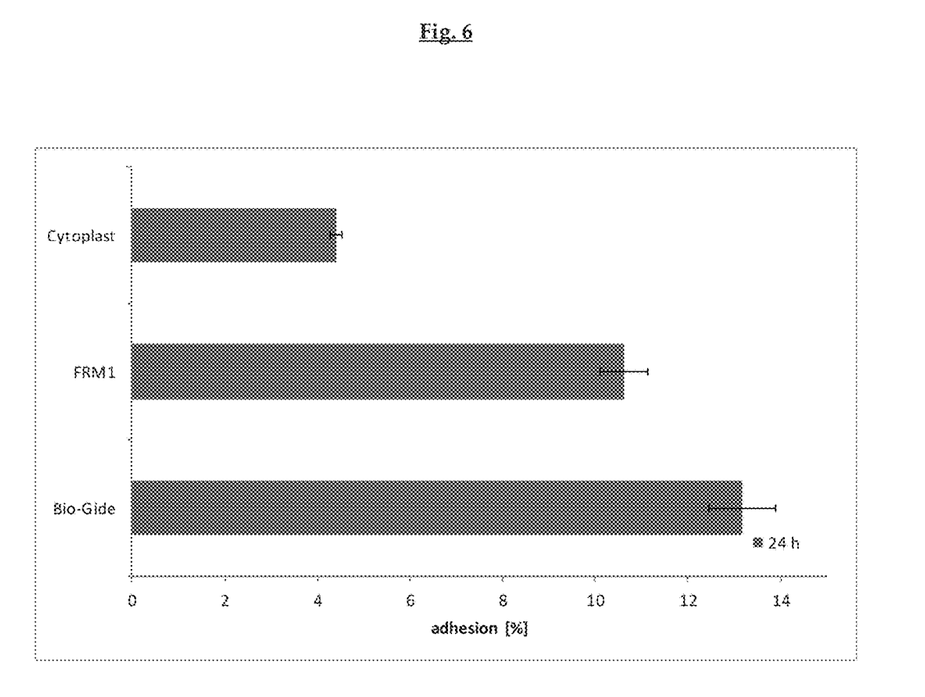
FIG. 6 is a column diagram of the % of human gingival fibroblasts that have adhered to the membrane after incubation for 24 hours in PBS at 37° C. for Geistlich Bio-Gide® collagen membrane, a prototype of the resorbable form stable membrane of the invention crosslinked by DHT (FRM) and the Cystoplast® PTFE. membrane (Keystone Dental).

The results obtained for the formstable resorbable membrane are represented in FIG. 5 which is a column diagram representing horizontally the % of cells capable to adhere on different types of dental membranes in percentage, the resorbable crosslinked form stable membrane of the invention and the Cystoplast® PTFE membrane (Keystone Dental).

FIG. 5 shows that adhesion to the resorbable crosslinked form stable membrane of the invention is about 10.5%, a value much closer to that of the Geistlich Bio-Gide® membrane of about 13% than to that of the Cystoplast® PTFE membrane of about 4%. The Geistlich Bio-Gide® membrane is well known for its good healing properties with a low rate of dehiscence (Zitzmann, Naef et al. 1997; Tal, Kozlovsky et al. 2008) or no excessive inflammation (Jung, 2012). This measured value of adhesion of human gingival fibroblasts to the resorbable crosslinked form stable membrane of the invention is predictive for soft tissue healing without adverse advents such as excessive inflammation or dehiscence.

(5) Measurement of the Elongation of the Elastic Pretensed Collagen Material Layers To determine the amount of tensioning of the collagen layers, the dry collagen layer is mounted to a tensioning ring (FIG. 2, part a) using the not yet tensioned springs (FIG. 2, part b). In the centre of the membrane at least 4 points, which are several centimetres apart from each other, are marked using a pencil or pen. The distance between each point is measured using a ruler. The measured distances are defined as the initial lengths between each point. The collagen layer is submerged in water and tensioned to the desired force. The collagen layer is incubated in water for 30 minutes. Due to the viscoelastic nature of most collagen layers, the tension reduces. Therefore, the collagen layers need to be tensioned again. After 30-40 minutes of incubation the distance between each point is measured with a ruler. The percentage of strain is determined by subtracting the initial length from the length after tensioning, divided by the initial length multiplied by 100.

Typical results such as to be in the linear region of the stress-strain curve are between 40 and 100% strain (elongation, stretching) for unsterile Geistlich Bio-tide.

Strain values measured by this method are not directly comparable to strain values obtained in a uniaxial elongation test.

(6) Measurement of the Thickness of Collagen Hydroxyapatite Plate and Final Prototype The thickness of the final prototypes or the collagen/hydroxyapatite plate "E" can be measured as described above or by using a sliding calliper.

(7) Analysis of the Mechanical Properties of Different Collagen Layers (FIG. 5)

To compare different sources of collagen layers and estimate their mechanical properties, standard uniaxial tensioning of wet samples was used. A general setup for such an analytical method is described in ASTM D882-09 "Standard Test Method for Tensile Properties of Thin Plastic Sheeting". Due to the high costs of the collagen membranes used, several parameters of the testing were adapted.

Samples were cut into rectangular sheets of e.g. 2×1 cm, prewetted in isotonic phosphate buffered saline and mounted to a tensile testing machine with a distance of 1 cm between each sample holder. The samples were tensioned at a constant speed of 33% of initial length per minute. The preforce, at which 100% initial length is recorded, was typically set to 50 kPa. The elongation of the sample was calculated using the distance between the two sample holders.

The stress-strain curves of FIG. 5 were thus obtained.

While the invention has been illustrated and described in details in the drawings and forgoing description, such illustration and description are to be considered illustrative or exemplary and not restrictive: the invention is not limited by the disclosed embodiments.

Other variations to the disclosed embodiments can be understood and effected by those skilled in the art in practicing the claimed invention, from a study of the drawings, the disclosure and the amended claims.

In the claims, the word "comprising" does not exclude other elements; the definite article "a" or "an" does not exclude a plurality.

INCORPORATION BY REFERENCE

All documents referenced herein are hereby incorporated by reference as if set forth in their entirety herein, as well as all references cited therein.

The invention claimed is:

1. A resorbable crosslinked form stable membrane which comprises a composite layer of collagen material and inorganic ceramic particles containing 1.5 to 3.5 weight parts of inorganic ceramic for 1 weight part of collagen material, sandwiched between two layers of elastic pretensed collagen material that do not contain inorganic ceramic particles, wherein the elastic pretensed collagen material is collagen material that has been stretched such as to be in the linear/elastic region of the stress-strain curve, the collagen material comprising 50-100% (w/w) collagen and 0-50% (w/w) elastin.

2. The resorbable crosslinked form stable membrane of claim 1, wherein the composite layer of collagen material and inorganic ceramic particles contains 2.0 to 3.0 weight parts of inorganic ceramic for 1 weight part of collagen material.

3. The resorbable crosslinked form stable membrane of claim 1, wherein the collagen material comprises 70-90% (w/w) collagen and 10-30% (w/w) elastin.

4. The resorbable crosslinked form stable membrane of claim 1, wherein the collagen material is derived from tissues of natural origin selected from the group of mammalian peritoneum or pericardium membrane, placenta membrane, small intestine submucosa (SIS), dermis, dura mater, ligaments, tendons, diaphragm, omentum and fascie of muscles or organs.

5. The resorbable crosslinked form stable membrane of claim 1, wherein the collagen material is derived from a porcine, bovine or equine peritoneum or pericardium membrane, small intestine mucosa (SIS) or muscle fascie.

6. The resorbable crosslinked form stable membrane of claim 1, wherein the elastic pretensed collagen material has an elastic modulus of 2 to 150 MPa.

7. The resorbable crosslinked form stable membrane of claim 1, wherein one of the layers of the elastic pretensed collagen material includes holes of 5 to 500 µm.

8. The resorbable crosslinked form stable membrane of claim 1, wherein the inorganic ceramic particles have a size of 150 to 500 µm.

9. The resorbable crosslinked form stable membrane of claim 1, wherein the inorganic ceramic is hydroxyapatite.

10. The resorbable crosslinked form stable membrane of claim 1, wherein the inorganic ceramic is hydroxyapatite bone mineral.

11. The resorbable crosslinked form stable membrane of claim 1, which is chemically crosslinked.

12. The resorbable crosslinked form stable membrane of claim 1, which is crosslinked by dehydrothermal treatment DHT.

13. A process for preparing a crosslinked resorbable crosslinked form stable membrane of claim 1, comprising the steps of:
   (a) Preparing a composite layer of inorganic ceramic particles and collagen material, optionally crosslinking that composite layer,
   (b) Assembling and glueing the composite layer of collagen material and inorganic ceramic particles between two layers of collagen material submitted to tensioning leading to a stretching of the collagen material in the linear region of the stress-strain curve, thereby giving a composite layer of collagen material and inorganic ceramic particles sandwiched between two layers of elastic pretensed collagen material, and
   (c) Crosslinking that composite layer of collagen material and inorganic ceramic particles sandwiched between two layers of elastic pretensed collagen material, followed by a hydrophilic making treatment wherein the hydrophilic making treatment comprises immersing the crosslinked composite layer of collagen material and inorganic ceramic particles sandwiched between two layers of elastic pretensed collagen material into a sodium chloride solution.

14. A bone implant comprising the resorbable crosslinked form stable membrane of claim 1, wherein said bone implant has suitable shape and dimensions to support bone formation, bone regeneration, bone repair and/or bone replacement at a non-containing dental bony defect site in a human or animal.

15. A method of treating human bone tissue in an oral cavity of a human or animal, comprising applying the resorbable crosslinked form stable membrane of claim 1 to the oral cavity of a human or animal in need of bone formation support, bone regeneration support, bone repair and/or bone replacement in the human patient's oral cavity, thereby effecting bone formation, bone regeneration, bone repair and/or bone replacement in the oral cavity of the human.

16. The method of claim 15, wherein the composite layer of collagen material and inorganic ceramic particles contains 2.0 to 3.0 weight parts of inorganic ceramic for 1 weight part of collagen material.

17. The method of claim 15, wherein the collagen material comprises 70-90% (w/w) collagen and 10-30% (w/w) elastin.

18. The method of claim 15, wherein the collagen material is derived from a porcine, bovine or equine peritoneum or pericardium membrane, small intestine mucosa (SIS) or muscle fascie.

19. The method of claim 15, wherein the inorganic ceramic is hydroxyapatite.

* * * * *